(12) United States Patent
Kubic, Jr. et al.

(10) Patent No.: US 11,708,342 B1
(45) Date of Patent: Jul. 25, 2023

(54) METHOD AND SYSTEM EMBODIMENTS FOR MAKING FURFURAL FROM HEMICELLULOSE SOURCE MATERIALS

(71) Applicant: Triad National Security, LLC, Los Alamos, NM (US)

(72) Inventors: William L. Kubic, Jr., Los Alamos, NM (US); Xiaokun Yang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 17/530,124

(22) Filed: Nov. 18, 2021

Related U.S. Application Data (60) Provisional application No. 63/118,501, filed on Nov. 25, 2020.

(51) Int. Cl.
*C07D 307/50* (2006.01)
*C13K 13/00* (2006.01)

(52) U.S. Cl.
CPC .......... *C07D 307/50* (2013.01); *C13K 13/002* (2013.01)

(58) Field of Classification Search
CPC .................................................. C07D 307/50
See application file for complete search history.

(56) References Cited

U.S. PATENT DOCUMENTS

| | | | |
|---|---|---|---|
| 2,379,332 | A | 6/1945 | Arnold |
| 2,818,413 | A | 12/1957 | Natta |
| 4,029,515 | A | 6/1977 | Kiminki et al. |
| 2019/0284151 | A1 | 9/2019 | Carlson et al. |

OTHER PUBLICATIONS

Agirrezabal-Telleria et al., "Dehydration of d-xylose to furfural using selective and hydrothermally stablearenesulfonic SBA-15 catalysts," *Applied Catalysis B: Environmental*, vol. 145, pp. 34-42, Nov. 19, 2012.

Anukam et al., "Studies on characterization of corn cob for application in a gasification process for energy production," *Journal of Chemistry*, vol. 2017, 9 pages, Jun. 11, 2017.

Biddy et al., "Chemicals from biomass: a market assessment of bioproducts with near-term potential," National Renewable Energy Laboratory Technical Report, Mar. 2016.

De Jong et al., "Overview of biorefineries based on co-production of furfural, existing concepts and novel developments," *International Journal of Chemical Reactor Engineering*, 8(1): 27 pages, Apr. 5, 2010.

Jiang et al., "Comprehensive evaluation of combining hydrothermal pretreatment (autohydrolysis) with enzymatic hydrolysis for efficient release of monosaccharides and ferulic acid from corn bran," *Industrial Crops & Products*, vol. 113, pp. 348-357, Feb. 12, 2018.

Nhien et al., "Techno-economic assessment of hybrid extraction and distillation processes for furfural production from lignocellulosic biomass" *Biotechnol Biofuels*, 10(81): Mar. 29, 2017.

Noureddini et al., "Dilute-acid pretreatment of distillers' grains and corn fiber," *Bioresource Technology*, 101(3): 1060-1067, Sep. 20, 2009.

Pointner et al., "Composition of corncobs as a substrate for fermentation of biofuels," *Agronomy Research*, 12(2): 391-396, May 2014.

Werpy et al., "Top value added chemicals from biomass vol. 1—results of screening for potential candidates from sugars and synthesis gas," Pacific Northwest National Laboratory National Renewable Energy Laboratory Office of Biomass Program, Aug. 2004.

Win, "Furfural—gold from garbage," *AU J.T.*, 8(4): 185-190, Apr. 2005.

*Primary Examiner* — Golam M Shameem
(74) *Attorney, Agent, or Firm* — Klarquist Sparkman, LLP (57) ABSTRACT

Disclosed herein are embodiments of a method for producing furfural from a hemicellulose source material. Also disclosed are embodiments of a system for carrying out the method. In particular embodiments, the method can be carried out without adding an extraneous mineral acid to facilitate pentose production from the hemicellulose source material and thus byproducts produced by the method can be used as animal feed.

12 Claims, 6 Drawing Sheets

METHOD AND SYSTEM EMBODIMENTS FOR MAKING FURFURAL FROM HEMICELLULOSE SOURCE MATERIALS

CROSS REFERENCE TO RELATED APPLICATION

This application claims the benefit of the earlier filing date of U.S. Provisional Patent Application No. 63/118,501, filed on Nov. 25, 2020, the entirety of which is incorporated herein by reference.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

The present disclosure is directed to embodiments of a method for making furfural from a hemicellulose source without having to add extraneous mineral acid.

BACKGROUND

Furfural is a bio-derived industrial chemical. The reported global furfural production was 370,000 tons in 2016 with a market value of $642 million and a projected market growth rate of 11% per year. Most furfural (90%) is converted into furfuryl alcohol, which is used for foundry-sand binder resins, corrosion-resistant fiber-reinforced plastics, corrosion resistant cements and mortars, wood protection, and so forth. Other uses of furfural are a solvent for extracting butadiene, and isoprene from $C_4$ and $C_5$ hydrocarbons, a reactive solvent and wetting agent, and a control agent for parasitic worms (nematodes). The United States (U.S.) Department of Energy (DOE) has identified furfural as one of the top 30 platform chemicals derived from biomass. However, furfural production in the U.S. is prohibitively expensive using current feedstocks and process technology. There exists a need in the art for improved furfural production methods that are efficient, cost effective, and that can be used in combination with various available feedstuffs and/or currently existing infrastructure.

SUMMARY

Disclosed herein are embodiments of a method for making furfural from hemicellulose source materials. In particular embodiments, the method comprises exposing a slurry comprising a hemicellulose source material and water to conditions sufficient to produce pentoses from the hemicellulose source material, thereby providing an aqueous mixture of residual biomass solids and the pentoses; filtering the residual biomass solids from the aqueous mixture to thereby isolate an aqueous filtrate comprising the pentoses; exposing the aqueous filtrate comprising the pentoses to a heterogeneous catalyst to produce an aqueous furfural-containing composition; exposing the aqueous furfural-containing composition to steam to promote stripping of a furfural-containing fluid from the aqueous furfural-containing composition; and condensing the furfural-containing fluid to produce an aqueous furfural-containing liquid.

The foregoing and other objects and features of the present disclosure will become more apparent from the following detailed description, which proceeds with reference to the accompanying figures.

DETAILED DESCRIPTION

Overview of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided.

Aqueous Furfural-Containing Composition: A composition comprising furfural, water, and byproducts obtained from exposing pentoses to a heterogeneous catalyst as described herein. Exemplary byproducts can include, but are not limited to, glucose and organic acids.

Cereal Grains: Seeds and/or grains obtained from grasses, such as (but not limited to) wheat, millet, rice, barley, oats, rye, triticale, sorghum, and maize (corn).

Extraneous Mineral Acid: An acid derived from one or more inorganic compounds and that forms hydrogen ions and a conjugate base when dissolved in water and that is affirmatively added during a process step of a method disclosed herein, or is affirmatively combined with any component and/or solution used or produced in the method embodiments disclosed herein. Put another way, an extraneous mineral acid is one that is not inherently produced during hydrolysis of a hemicellulose source material and instead is added during the method. Extraneous mineral acids can include sulfuric acid, hydrochloric acid, nitric acid, perchloric acid, boric acid, and the like.

Furfural-Containing Fluid: A fluid comprising a mixture of steam and furfural-containing vapors (e.g., vapor comprising furfural vapors and other volatile compounds). In some embodiments, the furfural-containing fluid can further comprise acetic acid, hydroxymethyl furfural, formic acid, levulinic acid, or combinations thereof.

Hemicellulose Source Material: A lignocellulose material comprising hemicellulose. In some embodiments, the hemicellulose source material comprises a hemicellulose content of 40 wt % or higher, such as 44 wt % or higher.

Heterogenous Catalyst: A catalyst that exists in a phase that is different from that of the reactant(s) exposed to the catalyst and/or that of the product(s) made using the catalyst. In particular embodiments, the heterogeneous catalyst is a solid phase catalyst.

Modifier Compound: A compound that can increase catalytic activity of a solid support and/or that can render an inert solid support catalytic by being combined with the inert solid support. In some embodiments, the modifier compound itself can be catalytic. In particular embodiments, the modifier compound is a poly(sulfonic acid), a functionalized sulfonic acid, or a combination thereof.

Organic Acid: Organic compound(s) with acid properties that are byproducts and/or remnants obtained from hydrolysis of a hemicellulose source material during hot water or acid extraction and that are not pentoses or other soluble organic compounds. In some embodiments, the organic acid is an organic acid formed upon hydrolysis of hemicellulose. In exemplary embodiments, the organic acid can be acetic acid, formic acid, levulinic acid, and uronic acids comprising d-glucuronic acid and/or 4-O-methyl-d-glucuronic acid.

Pentoses: Saccharide compounds comprising 5 carbon atoms that obtained from autohydrolysis of a hemicellulose source material. In some embodiments, the pentoses can be monomers or pentose oligomers. In some independent embodiments, the pentoses can comprise a mixture of monomers and/or oligomers of pentoses. In particular embodiments, pentoses include D- and/or L-arabinose, D- and/or L-lyxose, D- and/or L-ribose, D- and/or L-xylose.

Residual Biomass Solids: Solid materials that are byproducts and/or remnants obtained from autohydrolysis of a hemicellulose source material during hot water extraction and that are not pentoses.

Solid Acid Catalyst: An acid that does not dissolve in a reaction medium. In some embodiments, the solid acid catalyst is an acid that does not dissolve in water.

Solid Support: A component of a heterogenous catalyst. In some embodiments, the solid support can itself be a heterogenous catalyst. In some other embodiments, the solid support can be inert (e.g., not inherently catalytic) and can comprise a modifier compound and, together with the modifier compound, can be a heterogeneous catalyst. In some embodiments, the solid support has a high surface area. Exemplary solid supports can include, but are not limited to silica-based supports, zeolite supports a polystyrene-based exchange resin, or combinations thereof.

Structured Packing Component: A specially designed material with a regular structure for creating a large surface are for contact between to different fluid phases. In some embodiments, the structured packing component can contain or otherwise immobilize the heterogenous catalyst so as to increase the amount of fluid exposed to the heterogeneous catalyst.

Introduction

No significant quantities of furfural are currently produced in the United States because furfural production in the U.S. is prohibitively expensive using current feedstocks and process technology. Furfural can be produced from pentose compounds present in hemicellulose. In 1921, the first commercial-scale furfural process used oat hulls as the source of hemicellulose. Corn is the largest commercial crop raised in the U.S., so corncobs should be plentiful; however, the potential supply of corncobs depends on prices for farmers. For example, farmers need a price of $40-$120 per dry ton to make harvesting corncobs attractive with higher prices corresponding to larger supplies. And, to be successful, a domestic U.S. furfural plant should be profitable at world market prices. This is difficult, however, using current furfural production methods. As such, alternative feedstocks and process technology that reduces chemical consumption are needed if U.S.-produced furfural is to be competitive in the world market and a cost-effective platform chemical.

Disclosed herein are embodiments of a method for making furfural that facilitate cost-effective furfural production and that can be employed with various types of feedstocks and easily introduced into already-existing infrastructure (e.g., corn-to-ethanol plants, and the like). The disclosed method operates without the need for extraneous mineral acids that are affirmatively added during the method, which are used in traditional furfural production methods. As such, acidic wastewater and sulfates and other inorganic salts typically formed when using such extraneous mineral acids can be avoided. Also, the disclosed method embodiments produce by-products that can be recycled and used in the method and/or that serve as products for other industries. For example, residual biomass solids obtained from embodiments of the disclosed method can be used as animal feed (e.g., cattle feed). And, since affirmatively-added mineral acids are not used in the method, the biomass residue is not degraded and does not require any further purification and/or modification. System embodiments for carrying out method embodiments of the present disclosure are also described herein.

Embodiments

Disclosed herein are embodiments of a method from making furfural from a hemicellulose source material. In some embodiments, the method comprises an aqueous-phase hydrolysis of hemicellulose present in the hemicellulose source material to provide a composition comprising pentoses (e.g., pentose monomers and/or pentose oligomers), hexoses, and/or hexose oligomers, and organic acids) and residual biomass solids. The method can further comprise separating and removing the residual biomass solids from the composition to provide a pentose-containing composition; and exposing the pentose-containing composition to a heterogenous catalyst to produce furfural. In some embodiments, the method is a continuous method. In an independent embodiment, the method is a batch-wise method. Additional features of the method are described herein.

In some embodiments, the aqueous-phase hydrolysis of the hemicellulose source material comprises exposing a slurry comprising a hemicellulose source material and water to conditions sufficient to produce pentoses from the hemicellulose source material, thereby providing an aqueous mixture of residual biomass solids and the pentoses. In some embodiments, this can comprise exposing an aqueous slurry of hemicellulose source material to hot water extraction to facilitate obtaining pentoses from the hemicellulose source material. The hemicellulose source material can be any lignocellulosic-based source, such as (but not limited to) corn-based materials, other grain-based materials, sugarcane-based materials, wood hips, and/or waste from pulping processes. In particular embodiments, the hemicellulose source material is selected from a bran material (e.g., corn bran or bran from other cereal grains, such as sorghum and the like); a fiber material (e.g., corn fiber or fibers from other cereal grains, such as sorghum and the like); a bagasse material (e.g., sugarcane bagasse); a straw material (e.g., straw from cereal grains); a stover material (e.g., corn stover); or a cob-based material (e.g., corncobs); or any combination thereof. In representative embodiments, the hemicellulose source material is corn bran or corn fiber. In some embodiments, the water used in the hot water extraction can be obtained from reactions and/or steps of certain method embodiments that occur downstream relative to the hot water extraction process.

In particular embodiments, the hot water extraction comprises heating the slurry of hemicellulose source material and water at a temperature sufficient to promote hydrolysis (e.g., autohydrolysis) of hemicellulose present in the hemicellulose source material. In some embodiments, the temperature is not a temperature that promotes depolymerizing cellulose, starch and/or lignin that may be present in the hemicellulose source material. In particular embodiments, the hot water extraction process comprises heating the aqueous slurry at a temperature ranging from 150° C. to 245° C., such as 180° C. to 240° C., or 200° C. to 240° C., or 220° C. to 240° C. In particular embodiments, the aqueous slurry of the hemicellulose source material is heated at a temperature of 180° C., or 200° C., or 220° C., or 240° C. In particular embodiments, the hot water extraction promotes the formation of organic acids (e.g., glucuronic acid, acetic acid, or a combination thereof) and inorganic acids (e.g., phosphoric acid) that are not extraneous mineral acids, which can be used to facilitate further conversion of the hemicellulose course material to pentoses. The organic acids formed during the hot water extraction can be recycled for further use in the hot water extraction to thereby increase the reaction rate for the hydrolysis of the hemicellulose source material and/or yields of the pentoses obtained therefrom. As such, the method can be operated without the affirmative addition of extraneous mineral acids to the process stream or the aqueous slurry comprising the hemicellulose source material. In particular embodiments, the method does not comprise a step of adding an extraneous mineral acid at any point during the method and/or does not comprise a step of combining (or adding) an extraneous mineral acid with (or to) (i) any slurry comprising the hemicellulose source material and water; (ii) the hemicellulose source material; the water; (iii) the hydrolysis products from the hot water extraction; (iv) the aqueous mixture of residual biomass solids and the pentoses; or (v) any combination thereof. In such embodiments, the extraneous mineral acid can be sulfuric acid or another mineral acid that is not inherently produced during hydrolysis of the hemicellulose source material. After the hot water extraction, an aqueous mixture comprising residual biomass solids and pentoses is obtained.

The method further comprises removing residual biomass solids from the aqueous mixture comprising the residual biomass solids and the soluble products of hemicellulose hydrolysis to provide an aqueous filtrate comprising products of hemicellulose hydrolysis including pentose sugars (and oligomers thereof), hexose sugars (and oligomers thereof), organic acids, inorganic acids, or any combination thereof. In some embodiments, the method can comprise cooling the aqueous mixture comprising residual biomass solids and pentoses and then passing the mixture to a residual solids filter component as described herein so as to separate the aqueous phase comprising the pentoses from the residual biomass solids. In some embodiments, the method can further comprise combining the isolated residual biomass solids with clean water from an external source. This washing step can facilitate removing any residual sugars and/or dissolved chemicals from the residual biomass solids thereby maximizing the recovery of sugars and organic acids. If the hemicellulose source is corn bran or other biomass product suitable for animal feed, washing provides residual biomass solids that are also suitable as an animal feed. In yet some additional embodiments, the residual biomass solids obtained after the washing step can be dewatered so as to remove excess water. The dewatered residual biomass solids from corn bran and similar fibrous grain byproducts can be used as animal feed, or can be combined with solids from a corn-to-ethanol process, and then incorporated into dried distiller's grain and solubles (or "DDGS"). In some embodiments, the dewatered residual biomass solids can be dried, such as by using drying equipment used in the method embodiments disclosed herein or by using driers used in other processes with which the disclosed method can be combined (e.g., ethanol processing). In particular embodiments, the residual biomass solids and/or the dewatered residual biomass solids are free of sulfates or other potentially harmful residue. In some such embodiments, the residual biomass solids and/or the dewatered residual biomass solids are free of sulfates because the method is free of any extraneous mineral acid addition.

The method also comprises further treating the aqueous filtrate comprising the pentoses that is obtained from the filtration step used to remove the residual biomass solids. In some embodiments, this can comprise exposing the aqueous filtrate comprising the pentoses to a catalyst to produce an aqueous furfural-containing composition. In some embodiments, this can comprise passing the aqueous filtrate to a furfural reactive distillation tower comprising the catalyst. In particular embodiments, the furfural reactive distillation tower can be a fixed bed reactor. In some additional embodiments, the aqueous filtrate, which comprises the pentoses, can be combined with any filtrate obtained from the dewatering step described above and then passed to the furfural reactive distillation tower.

In the furfural reactive distillation tower, any pentoses present in the aqueous filtrate can be dehydrated in the presence of the catalyst to provide furfural. In particular embodiments, the aqueous filtrate comprises pentose sugars capable of being converted to furfural. For example, the aqueous filtrate can comprise xylose, arabinose, and other pentose sugars and pentose oligomers that may be present in the hemicellulose. Dehydrating the pentoses to furfural can comprise exposing the aqueous filtrate to a catalyst. In particular embodiments, the catalyst is a heterogenous catalyst. The heterogeneous catalyst can be a solid acid catalyst comprising a solid support. The solid support can, itself, be catalytic. In some embodiments, however, the solid support can be modified with a modifier compound to provide catalytic activity. In some such embodiments, a surface of the solid support can be modified with the modifier compound and/or the modifier compound can be embedded throughout the solid support. In some embodiments, the solid support can be a silica-based support, such as a mesoporous silica (e.g., SBA-15 or other SBA silica supports) or silica of another form (e.g., amorphous, crystalline, or the like); a zeolite material, such as an aluminosilicate, a silicoaluminophosphate, an Sn-Beta zeolite, an H-Beta zeolite, a mordenite zeolite, or the like; a polystyrene-based exchange resin; or combinations thereof. In some embodiments, the modifier compound can be a poly(sulfonic acid), such as an styrene-based poly(sulfonic acid) or an vinyl-based poly(sulfonic acid); or a functionalized sulfonic acid, such as an arenesulfonic acid or a propylsulfonic acid. In representative embodiments, a heterogenous catalyst comprising arene-sulfonic acid-modified SBA-15 or poly(sulfonic acid)-modified SBA-15 is used. In some embodiments, the dehydration step can be conducted at temperatures above ambient temperature, such as at temperatures ranging from 100° C. to 250° C., or 150° C. to 225° C., or 180° C. to 200° C.

In some embodiments, the method can comprise extracting the furfural from the aqueous furfural-containing composition produced in the furfural reactive distillation tower to avoid and/or suppress condensation products and/or resinification products produced by undesired condensation reactions between furfural and reaction side products and/or any self-condensation of the furfural. In particular embodiments, steam stripping conditions can be used to extract furfural-containing vapors from the aqueous furfural-containing composition contained in the furfural reactive distillation tower. In some such embodiments, steam is introduced into the bottom of the furfural reactive distillation tower so that it flows upward in a direction that is countercurrent to the flow path of the aqueous filtrate comprising the pentoses, which flows in a downward direction from the top of the furfural reactive distillation tower. A furfural-containing fluid is then emitted from the furfural reactive distillation tower. This resulting furfural-containing fluid comprises furfural-containing vapors that are then condensed to provide an aqueous furfural-containing liquid. Furfural can then be isolated from the aqueous furfural-containing liquid using a separation step, such as solvent extraction and/or distillation (e.g., azeotropic distillation).

In one embodiment, the aqueous furfural-containing liquid is exposed to a solvent to promote collection of the furfural in the solvent. Furfural present in the aqueous furfural-containing liquid is collected in the solvent and the separate aqueous phase that is obtained after furfural removal can be treated to remove any residual solvent and then discarded as wastewater. In embodiment comprising a solvent treatment step, the separate aqueous phase is passed through a solvent stripper to separate any residual solvent that may be present in the separate aqueous phase.

In some embodiments, the solvent is an organic solvent, such as a hydrocarbon solvent, a halogenated solvent, an alcohol solvent, a ketone-containing solvent, or any combinations thereof. In particular embodiments, the organic solvent is selected from an aromatic hydrocarbon solvent (e.g., toluene; benzene; or a xylene, such as p-xylene, o-xylene, m-xylene, or any combination thereof), a chlorinated solvent (e.g., butyl chloride), an alcohol solvent (e.g., 1-butanol, 2-butanol, 4-methyl-2-butanol, or cyclohexanol), or a ketone-containing solvent (e.g., methyl isobutylene ketone, or acetophenone). In representative embodiments, the solvent is toluene. The furfural-containing solvent is then distilled to separate the furfural from the solvent. In some embodiments, distilling the furfural-containing solvent can comprise using a standard distillation technique, a reduced pressure distillation technique, an azeotropic distillation technique, a steam distillation technique, or other another distillation technique suitable for separating furfural from the solvent.

In another embodiment, the aqueous furfural-containing liquid can be fed to an azeotropic distillation column in which the bottoms product is wastewater and the distillate is a two-phase mixture comprising a water-rich phase containing dissolved furfural, which is recycled to the distillation column as reflux, and a furfural-rich phase containing dissolved water. The furfural-rich phase is fed to a second azeotropic distillation column in which the bottoms product is furfural, and the distillate is the same two liquid phases produced by the first column. The organic phase is recycled to the second distillation column and the aqueous phase is combined with the reflux for the first column. In some embodiments, a third distillation can be added to remove polymers and other heavy contaminants from the furfural. In other embodiments, the second column removes furfural as a sides stream with the bottoms product being heavy contaminants.

In particular embodiments, the method comprises the following: exposing a slurry comprising a hemicellulose source material and water to conditions sufficient to produce pentoses from the hemicellulose source material, thereby providing an aqueous mixture of residual biomass solids and the pentoses; filtering the residual biomass solids from the aqueous mixture to thereby isolate an aqueous filtrate comprising the pentoses; exposing the aqueous filtrate comprising the pentoses to a heterogeneous catalyst to produce an aqueous furfural-containing composition; exposing the aqueous furfural-containing composition to steam to promote stripping of a furfural-containing fluid from the aqueous furfural-containing composition; and condensing the furfural-containing fluid to produce an aqueous furfural-containing liquid.

In some embodiments, the conditions sufficient to produce pentoses from the hemicellulose source material comprise heating the slurry at a temperature sufficient to promote hydrolysis of hemicellulose present in the hemicellulose source material.

In any or all of the above particular embodiments, the temperature ranges from 150° C. to 245° C.

In any or all of the above particular embodiments, the hemicellulose source material is corn bran, sorghum, corn fiber, sugarcane bagasse, corn stover, corncobs, straw from cereal grains, or any combination thereof.

In any or all of the above particular embodiments, the heterogenous catalyst is a solid acid catalyst and the solid acid catalyst comprises a solid support selected from a silica-based support, a zeolite catalyst, a polystyrene-based exchange resin, and any combination thereof.

In any or all of the above particular embodiments, the solid acid catalyst further comprises a modifier compound that is embedded within the solid support or that is positioned on the surface of the solid support, wherein the modifier compound is a poly(sulfonic acid) or a functionalized sulfonic acid.

In any or all of the above particular embodiments, the solid acid catalyst comprises a mesoporous silica support and modifier compound that is an arene-sulfonic acid, a poly(sulfonic acid), or a combination thereof.

In any or all of the above particular embodiments, the heterogeneous catalyst is embedded in and/or on a surface of a structured packing component.

In any or all of the above particular embodiments, condensing the furfural-containing fluid comprises passing the furfural-containing fluid through a condenser.

In any or all of the above particular embodiments, the method further comprises separating the furfural from the aqueous furfural-containing liquid, wherein separating the furfural from the aqueous furfural-containing liquid comprises using solvent extraction or azeotropic distillation.

In any or all of the above particular embodiments, the solvent extraction comprises exposing the aqueous furfural-containing liquid to a solvent.

In any or all of the above particular embodiments, the method further comprises treating a separate aqueous phase produced from the solvent extraction by passing the separate aqueous phase through a solvent stripper to separate any residual solvent that may be present in the separate aqueous phase.

In any or all of the above particular embodiments, the method further comprises recycling organic acids formed from the hydrolysis of the hemicellulose back to the slurry so as to promote forming additional pentoses.

In any or all of the above particular embodiments, the method further comprises treating the residual biomass solids to obtain an animal feedstock.

In any or all of the above particular embodiments, treating the residual biomass solids comprises washing the residual biomass solids and/or exposing the residual biomass solids to a dewatering device.

In any or all of the above particular embodiments, treating further comprises a drying step.

In any or all of the above particular embodiments, the method does not comprise adding an extraneous mineral acid to the slurry comprising the hemicellulose source material; the hemicellulose source material; the water; the pentoses; the aqueous mixture of residual biomass solids and the pentoses; or any combination thereof.

Also disclosed herein are particular embodiments of a method comprising: heating a slurry comprising (i) a bran material, a fiber material, or a combination thereof, and (ii) water at a temperature ranging from 150° C. to 245° C. to produce pentoses selected from xylose, arabinose, and/or other sugars from the bran material and/or the fiber material, thereby providing an aqueous mixture of residual bran and/or fiber solids and the pentoses; recycling any organic acids produced from the bran material and/or the fiber material so as to expose the slurry to the organic acids; filtering the residual bran and/or fiber solids from the aqueous mixture to thereby isolate an aqueous filtrate comprising the pentoses; treating the residual bran and/or fiber solids to obtain an animal feedstock; exposing the aqueous filtrate comprising the pentoses to a heterogeneous catalyst comprising a mesoporous silica support modified with an arene-sulfonic acid or a poly(sulfonic acid) to produce an aqueous furfural-containing composition; exposing the aqueous furfural-containing composition to steam to promote stripping of furfural-containing vapors from the aqueous furfural-containing composition thus providing a furfural-containing fluid; and condensing the furfural-containing fluid to provide an aqueous furfural-containing liquid.

In any or all of the above particular embodiments, the method further comprises exposing the furfural-containing liquid to a solvent extraction or azeotropic distillation to isolate furfural from the furfural-containing liquid.

In any or all of the above particular embodiments, the method is performed batch-wise or as a continuous method.

Also disclosed herein are embodiments of a system for producing furfural from a hemicellulose source material. In some embodiments, the system is a continuous flow system or a batch-wise system. Physical components and various flow loops of system embodiments are described in more detail below.

In particular embodiments, the system comprises a tank configured to house a slurry comprising a hemicellulose source material and water, wherein the container is fluidly coupled to a water source and is physically coupled to a container that houses the hemicellulose source material; a reactor configured to house the slurry and maintain it at a temperature sufficient to produce pentoses from the hemicellulose source material, wherein the reactor is fluidly connected to tank; a filter component configured to separate residual biomass solids from an aqueous mixture comprising the residual biomass solids and the pentoses, wherein the filter is fluidly coupled to the reactor; a distillation tower configured to house (i) a heterogenous catalyst that converts the pentoses to furfural; and (ii) a solid packing component, wherein the distillation tower is fluidly coupled to the filter and a steam source; and one or more additional components configured to separate and/or isolate the furfural.

In some embodiments, the one or more additional components configured to separate and/or isolate the furfural includes a furfural condenser configured to condense a furfural-containing fluid emitted by the distillation tower to an aqueous furfural-containing liquid; a furfural extractor configured to extract furfural from the aqueous furfural-containing liquid produced by the furfural condenser; a distillation component configured to separate the furfural from a solvent via distillation; a solvent stripper configured to purify solvent for use in the furfural extractor; a distillation apparatus configured for azeotropic distillation to isolate furfural from the aqueous furfural-containing liquid; and/or any combination thereof.

In particular embodiments, the system comprises a slurry mixing tank, a residual biomass solids filter component, a hemicellulose extraction reactor, a furfural reactive distillation tower, a furfural condenser, a furfural extractor, a furfural distillation column, one or more introduction lines for introducing materials into the system (e.g. for introducing hemicellulose source material, steam, wash water, and the like), and one or more exit lines for removing materials from the system (e.g., for removing furfural from the system or removing byproducts and/or waste materials from the system). In some embodiments, the system can further comprise a residual biomass solids wash tank, a dewatering device (e.g., a dewatering screw press), a solvent stripper column, and one or more pumps, condensers, valves, heat exchangers, and the like to facilitate temperature control, phase modifications of any fluid passing through the system, and/or flow through components of the system.

In a particular exemplary embodiment, the system comprises: the tank; the reactor; the filter; the distillation tower; a furfural condenser configured to condense the furfural-containing fluid emitted by the distillation tower to an aqueous furfural-containing liquid, wherein the furfural condenser is fluidly coupled to the distillation tower; and (i) a furfural extractor configured to extract furfural from the aqueous furfural-containing liquid produced by the furfural condenser, wherein the furfural extractor is fluidly coupled to the furfural condenser; (ii) a distillation column configured to separate the furfural from a solvent via distillation, wherein the distillation column is fluidly coupled to the furfural extractor; and (iii) a solvent stripper configured to purify solvent for use in the furfural extractor, wherein the solvent stripper is fluidly coupled to the furfural extractor and the distillation column; or (iv) a distillation apparatus configured to isolate furfural from the aqueous furfural-containing liquid produced by the furfural condenser via azeotropic distillation.

In any or all of the above exemplary embodiments, the system further comprises the heterogenous catalyst and the solid packing component.

In any or all of the above embodiments, the system further comprises a wash tank fluidly coupled to the filter; and a dewatering device that is fluidly coupled to the wash tank.

Figure 1:
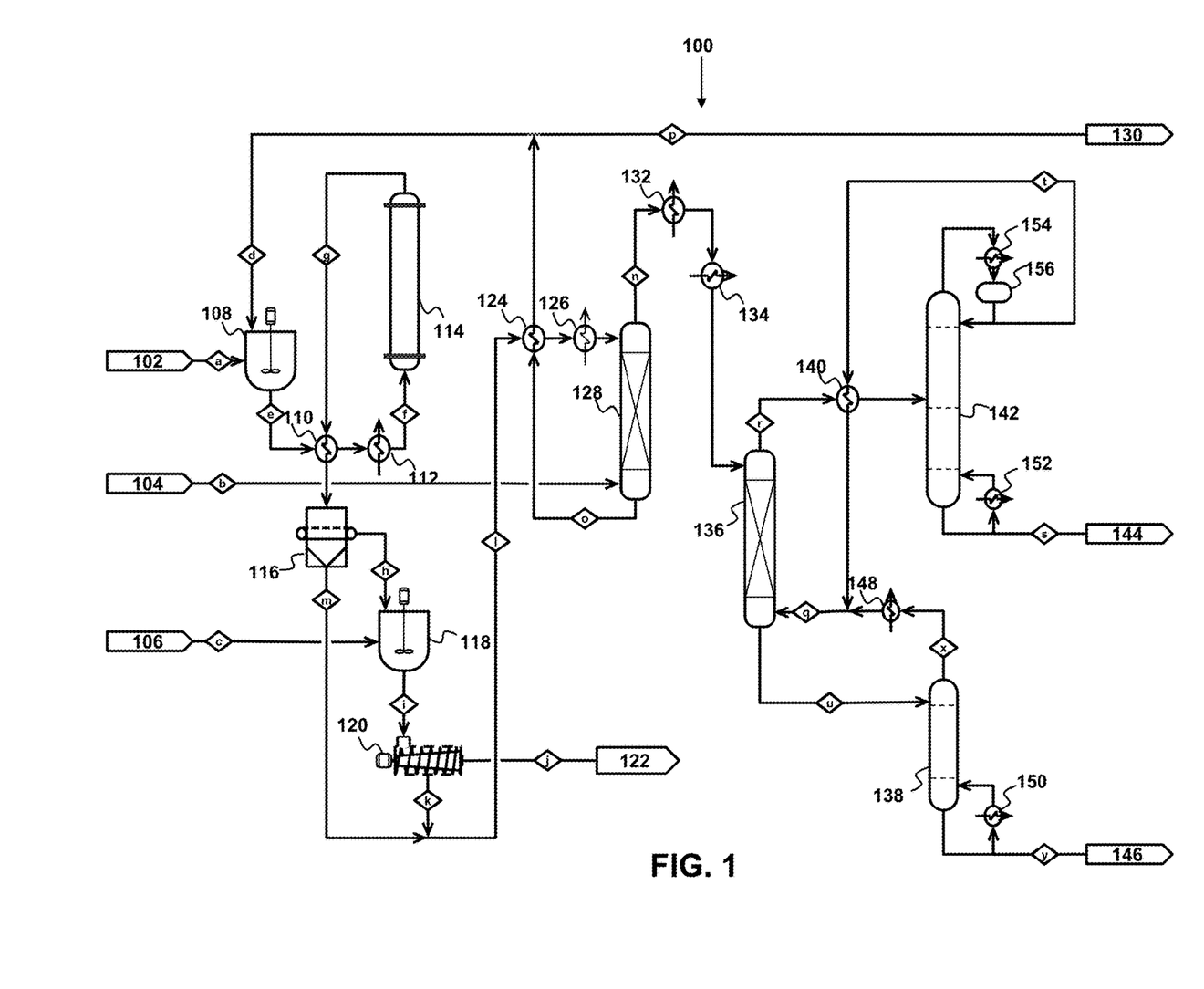
FIG. 1 is a schematic diagram showing a representative system for converting hemicellulose source material to furfural.

A non-limiting exemplary system is shown by FIG. 1. With reference to FIG. 1, system 100 comprises three introduction lines, including hemicellulose introduction line 102, steam introduction line 104, and wash water introduction line 106. The hemicellulose source material is introduced into the system via hemicellulose introduction line 102 and flow path "a." Steam used in the downstream steps described herein is introduced into the system via steam introduction line 104 and flow path "b" and wash water used to wash residual biomass solids produced in the method is introduced via wash water introduction line 106 and flow path "c." The system also comprises aqueous slurry mixing tank 108, which is a tank in which the aqueous slurry of hemicellulose source material is made by combining water recycled from downstream processes (added via flow path "d") and the hemicellulose source material.

The aqueous slurry is passed from aqueous slurry mixing tank 108 via flow path "e" through heat exchangers 110 and 112, which heat the aqueous slurry to a temperature sufficient to promote the hot water extraction of pentoses from the hemicellulose source material. Flow path "f" delivers the heated aqueous slurry to hemicellulose extraction reactor 114, wherein the hot water extraction occurs. The resulting mixture comprising the pentoses and residual biomass solids is removed from hemicellulose extraction reactor 114 and flows via flow path "g" to residual biomass solids filter 116.

Residual biomass solids are separated from the pentoses in residual biomass solids filter 116 and are passed from the filter to wash tank 118 via flow path "h," where the residual biomass solids are washed with wash water introduced via wash water introduction line 106 to remove byproducts and/or any residual sugar products. The washed residual biomass solids are then delivered to dewatering screw press 120 via flow path "i" where water is removed from the solids to provide solids suitable for animal feed, which are removed from the system via solids exit line 122 via flow path "j."

Excess water from dewatering screw press 120 is delivered via flow path "k" to flow path "I," where it is combined with filtrates from residual biomass solids filter 116, which are delivered to flow path "l" via flow path "m." The filtrates from residual biomass solids filter 116 include the extracted pentoses. The combined filtrates are then heated by passing through heat exchangers 124 and 126, which are positioned in series.

The heated fluid is then introduced into furfural reactive distillation tower 128, which houses the catalyst used to dehydrate the pentoses to furfural. In some embodiments, the catalyst can be free-form or it can be a supported catalyst. In embodiments that use a supported catalyst, the catalyst can be embedded in or coated on a support material. In particular embodiments, the catalyst is embedded in and/or coated on a structured packing component. In some embodiments, the structured packing component can be a structure capable of exposing the catalyst to the fluid containing the pentoses. The structured packing provides a large surface area, which enhances heat and mass transfer, while minimizing pressure drop. In particular embodiments, the structured packing component can be a packing sold by Sulzer or Koch-Glitsch. In some embodiments, the structured packing component is a Sulzer Katapak packing or a Koch-Glitsch KATAMAX® packing.

Steam introduced via steam introduction line 104 is added to furfural reactive distillation tower 128 via flow path b and is configured to flow from the bottom of the tower to the top, opposite the direction of the fluid comprising the pentoses. Using this configuration, the steam can strip furfural-containing vapors (such as furfural-containing vapors present in the furfural-containing fluid) from the fluid as it is produced by contact with the catalyst. As discussed herein, such embodiments of steam stripping can facilitate minimizing secondary reactions between any furfural product and byproducts of reactions that occur with the pentoses.

The resulting furfural-containing fluid produced from furfural reactive distillation tower 128 exits the tower via flow path "n," where it continues through the system. The fluid from which the furfural-containing vapors (e.g., such vapors present in the furfural-containing fluid) is stripped exits furfural reactive distillation tower 128 via flow path "o," where it is passed through heat exchanger 124. Some of the fluid is then added to flow path "d" for use in aqueous slurry mixing tank 108 and some of the fluid is purged from the system via flow path "p" and exit line 130. This purging can further facilitate removing excess water that is not needed for the hot water extraction and further facilitates removing excess acid and/or byproducts from the preceding process steps.

The furfural-containing fluid that exits furfural reactive distillation tower 128 (typically through the top of the tower) is directed to condenser 132, where the furfural-containing fluid (which comprises furfural-containing vapors) is condensed to provide an aqueous furfural-containing liquid. The aqueous furfural-containing liquid is then cool in heat exchanger 134. In particular embodiments, the cooled aqueous furfural-containing liquid can be passed to furfural extractor 136. In particular embodiments, the cooled aqueous furfural-containing liquid is introduced into the top of furfural extractor 136 where it is exposed to a solvent for furfural extraction. The solvent is introduced into the bottom of furfural extractor 136 via flow path "q," which provides recycled solvent from solvent stripper 138. The solvent flows up furfural extractor 136 and is able to extract furfural from the furfural-containing fluid, which flows down the furfural extractor in the opposite direction. The furfural-containing solvent exits furfural extractor 136 via flow path "r" and is then pre-heated in heat exchanger 140 and fed into furfural distillation column 142. Distillation is used to separate the furfural from the solvent and the furfural product exits the system via flow path "s" and exit line 144.

The solvent is expelled from furfural distillation column 142 via flow path "t," and passes through heat exchanger 140 where it is pre-heated and is then recycled back to furfural extractor 136. In some embodiments, the aqueous phase from furfural extractor 136 can comprise residual solvent. This solvent can be stripped from the aqueous phase by passing it through solvent stripper 138 by passing it from furfural extractor 136 to the solvent stripper via flow path "u." Water from solvent stripper 138 can be expelled as wastewater via flow path "v" and exit line 146 and/or can be used to produce steam, which can be reintroduced into solvent stripper 138. Solvent from solvent stripper 138 is then introduced into the process as discussed above via flow path "x" and after passing through heat exchanger 148.

In yet other embodiments, the cooled aqueous furfural-containing liquid can be fed into an azeotropic distillation column in which the bottoms product is wastewater and the distillate is a two-phase mixture comprising a water-rich phase containing dissolved furfural, which is recycled to the distillation column as reflux, and a furfural-rich phase containing dissolved water. The furfural-rich phase is fed to a second azeotropic distillation column in which the bottoms product is furfural, and the distillate is the same two liquid phases produced by the first column. The organic phase is recycled to the second distillation column and the aqueous phase is combined with the reflux for the first column. In some embodiments, a third distillation can be added to remove polymers and other heavy contaminants from the furfural. In other embodiments, the second column removes furfural as a sides stream with the bottoms product being heavy contaminants.

In some embodiments, the system can further comprise additional components that facilitate flow through the system and/or management of byproducts and/or reagents, such as pumps, valves, additional heat exchangers for converting steam (e.g., heat exchangers 150 and 152), heat exchangers for cooling solvent (e.g., heat exchanger 154) and/or drums for solvent storage (e.g., horizontal drum 156). Additional features of other optional system components are illustrated schematically in FIGS. 4-6.

Figure 4:
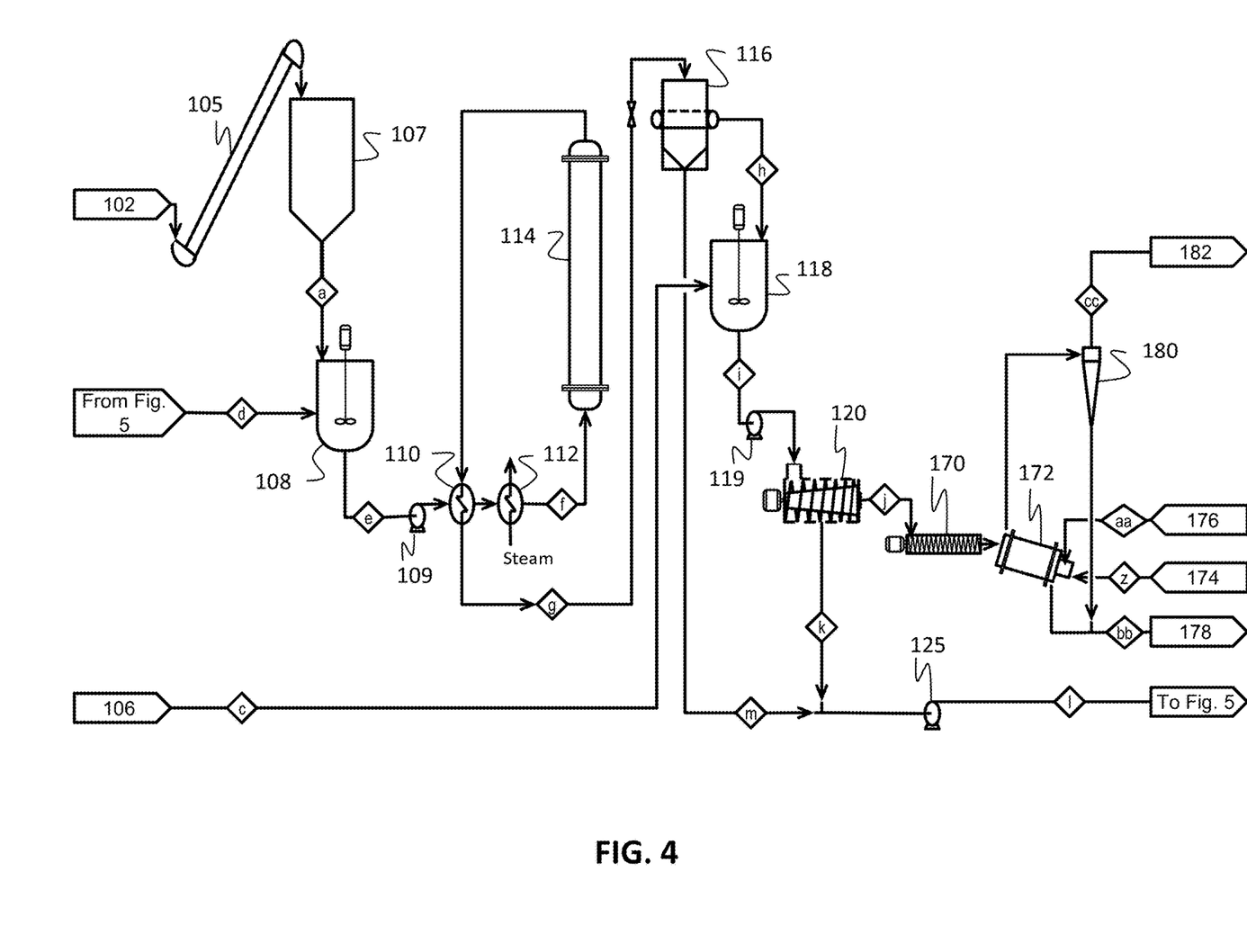
FIG. 4 is a schematic diagram showing optional system components that can be used to provide animal feed from residual biomass solids obtained in a method embodiment.

FIG. 4 shows a process flow diagram of a method and system embodiment of the present disclosure. With reference to FIG. 4, a hemicellulose source material is introduced into the system via a hemicellulose introduction line 102 to conveyor or elevator 105, which transfers the material to feed bin 107 for temporary storage. The hemicellulose source material is transferred from feed bin 107 via flow path "a" to aqueous slurry mixing tank 108, were it is combined with water recycled from downstream processes via flow path "d." The aqueous slurry exits aqueous slurry mixing tank 108 via flow path "e" and is pumped with slurry pump 109 through heat exchanger 110, which partially heats the slurry with hot effluent from hemicellulose extraction reactor 114 and steam heated heat exchanger 112. The effluent of heat exchanger 112 flows via flow path "f" to hemicellulose extraction reactor 114. The effluent from hemicellulose extraction reactor 114 is cooled in heat exchanger 110 with cool aqueous slurry. The cooled effluent flows via flow path "g" to a residual biomass solids filter 116. Residual biomass solids filter 116 separates the residual biomass solids from the aqueous pentose solution. The residual biomass solids are sent vis flow path "h" to wash tank 118, where they are mixed with wash water from wash water introduction line 106 via flow path "c." Slurry pump 119 pumps the contents of wash tank 118 to dewatering screw press 120. Wet residual biomass solids are fed to screw conveyor 170 via flow path "j" and fed to rotary drum drier 172. Natural gas supplied through natural gas introduction line 174 and combustion air supplied through combustion air introduction line 176 are fed to rotary drum 172 via flow paths "aa" and "z," respectively, where the natural gas is combusted hot gas to the drier. Hot gas exiting rotary drum drier 172 is fed to cyclone 180 to remove any entrained solids. The hot combustion gas exits cyclone 180 and the process via flow path "cc" and combustion gas exit line 182. Residual biomass solids from rotary drum drier 172 and cyclone 182 are combined and exit the process via flow path "bb" and dried biomass residue line 178. Excess water from dewatering screw press 120 is delivered via flow path "k" to flow path "m" where it is combined with the filtrate from residual biomass solids filter 116.

Figure 5:
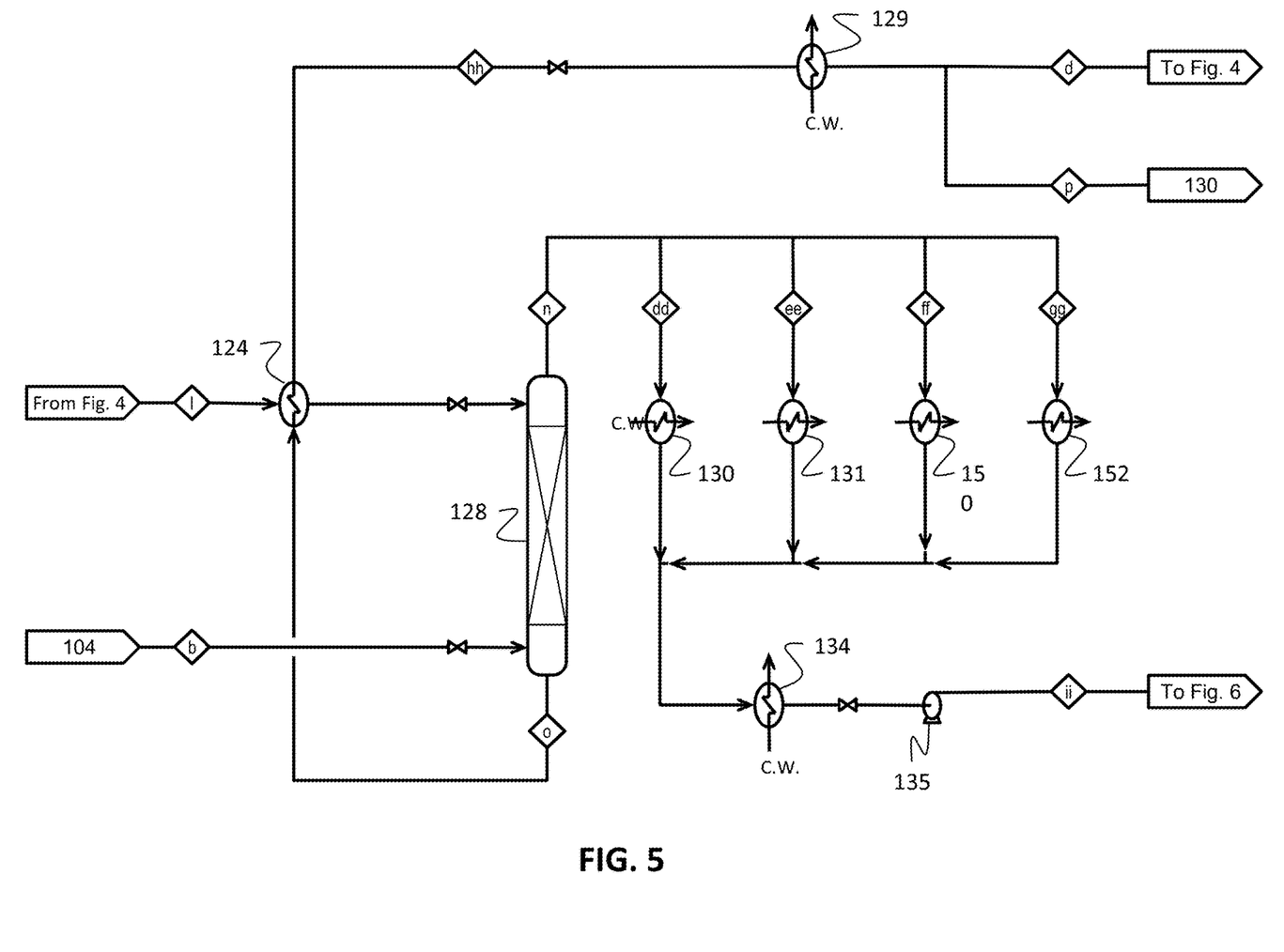
FIG. 5 is a schematic diagram showing optional system components and flow paths that can be used in combination with a furfural reactive distillation tower.

FIG. 5 provides an extension of the flow diagram of FIG. 4. With reference to FIG. 5, filtrate pump 125 (from FIG. 4) pumps the combined aqueous solution via flow path "l" through furfural reactor heat exchanger 124 to furfural reactive distillation tower 128. Furfural reactor heat exchanger 124 preheats the feed to furfural reactive distillation tower 128 with hot liquid effluent from the tower. Pentose sugars are dehydrated to furfural in furfural reactive distillation tower 128. Steam introduced via steam introduction line 104 is fed to the bottom of furfural reactive distillation tower 128 via flow path "b." Steam supplies heat to the distillation tower and strips the furfural from the aqueous pentose containing solution. The aqueous solution depleted of pentose sugars exits the bottom of furfural reactive distillation tower 128 via flow path "o" and is cooled in furfural reactive distillation column heater 124. The cooled solution is then transferred via flow path "hh" to recycle cooler 129. The depleted aqueous pentose containing solution is then split. A major part of the aqueous solution is recycled via flow path "d" to aqueous slurry mixing tank 108 in FIG. 4 via flow path "d." The remaining portion is wastewater that is purged from the process via flow path "p" and purge exit line 130. The purge is used to remove excess water and prevent contaminants from accumulating in the process. Steam containing furfural exits furfural reactive distillation tower 128 via flow path "n." The furfural containing steam is then split into four parts. One part is sent via flow path "ff" to furfural distillation column reboiler 150, where it is condensed and supplies heat to the reboiler. A second part is sent via flow path "gg" to solvent stripper reboiler 152, where it is condensed and supplies heat to the reboiler. A third part is sent via flow path "ee" to boiler feed water heater 131, where is condensed and heats the boiler feed water. The fourth part is sent via flow path "dd" to water cooled furfural condenser 130, where it is condensed. The aqueous furfural containing condensate from these four heat exchangers is combined and subcooled in aqueous furfural condensate cooler 134 and the cooled condensate is introduced to the top if furfural extractor 136 (see FIG. 6) with aqueous condensate pump 135 via flow path "ii."

Figure 6:
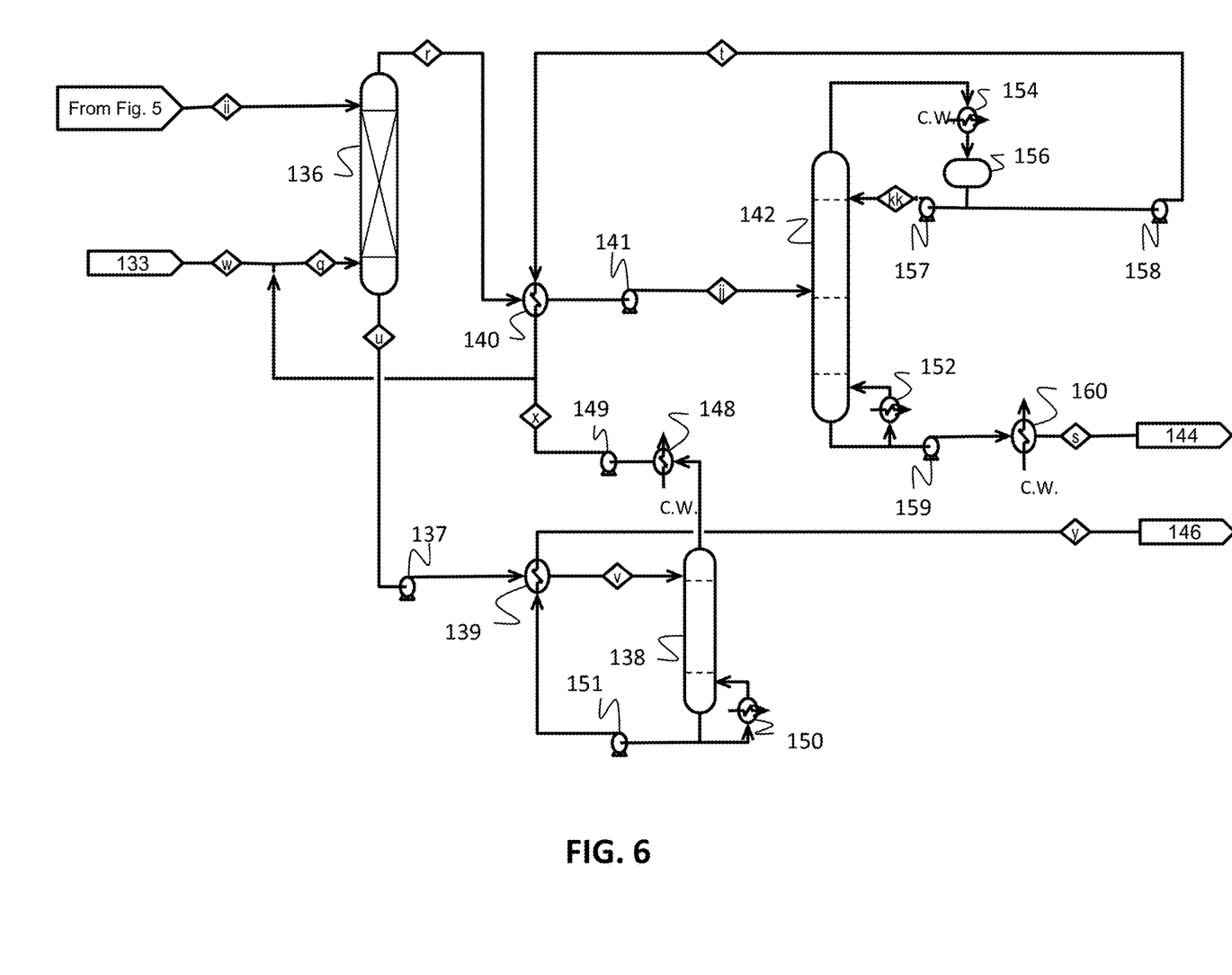
FIG. 6 is a schematic diagram showing optional system components and flow paths that can be used in combination with a furfural distillation column and/or a solvent stripper.

FIG. 6 shows an extension of the flow process diagram of FIGS. 4 and 5. With reference to FIG. 6, toluene, the solvent for the liquid-liquid extraction, is introduced to the bottom of furfural extractor 136 via flow path "q." The toluene flows counter current to the aqueous furfural containing condensate. The furfural diffuses from the aqueous phase into the toluene solvent. The toluene solvent exits furfural extractor at the top via flow path "r" and is heated in furfural distillation column feed heater 140. The furfural distillation column feed is heated with warm distillate from furfural distillation column 142. The warm furfural containing toluene solvent is pumped into furfural distillation column 142 with furfural distillation column feed pump 141 via flow path "jj." The more volatile toluene is the distillate and furfural is the bottoms product. Toluene vapors exit the top of furfural distillation column 142 and are condensed in furfural distillation column condenser 154 and accumulate in furfural distillation column reflux drum 156. A portion of the condensed toluene is recycled to the top of furfural distillation column 142 as reflux with furfural distillation column reflux pump 157 via flow path "kk." The remaining portion of the condensed toluene is pumped to furfural distillation column feed heater 140 with solvent recycle pump 158 to furfural distillation column feed heater 140, where it is cooled, via flow path "t" and delivered to flow path "q." The aqueous raffinate exiting the bottoms of furfural extractor 136 contains toluene in excess of allowable discharge limits. Solvent stripper 138 reduces the toluene content of the water below the allowable limit. The aqueous raffinate is pumped from solvent stripper 138 via flow path "u" with raffinate pump 137. The raffinate is heated in solvent stripper feed heater 139 with the bottom product of solvent stripper 138 and introduced to the top of the stripper via flow path "v." Vapor from the top of solvent stripper 138 are condensed in solvent stripper condenser 148 and pumped with solvent stripper condensate pump 149 via flow path "x" to flow path "q." Small quantities of toluene solvent are lost from the process in the furfural product and the bottom product of solvent stripper 138. Makeup toluene is introduced to the process toluene introduction line 133 and delivered to flow path "q" via flow path "w." The bottom product of solvent stripper 138 is wastewater, which is removed from the column with wastewater pump 151 and pumped through solvent stripper feed heater 139. The wastewater exist the process via flow path "y" and wastewater exit line 146.

EXAMPLES

Example 1

Figure 2:
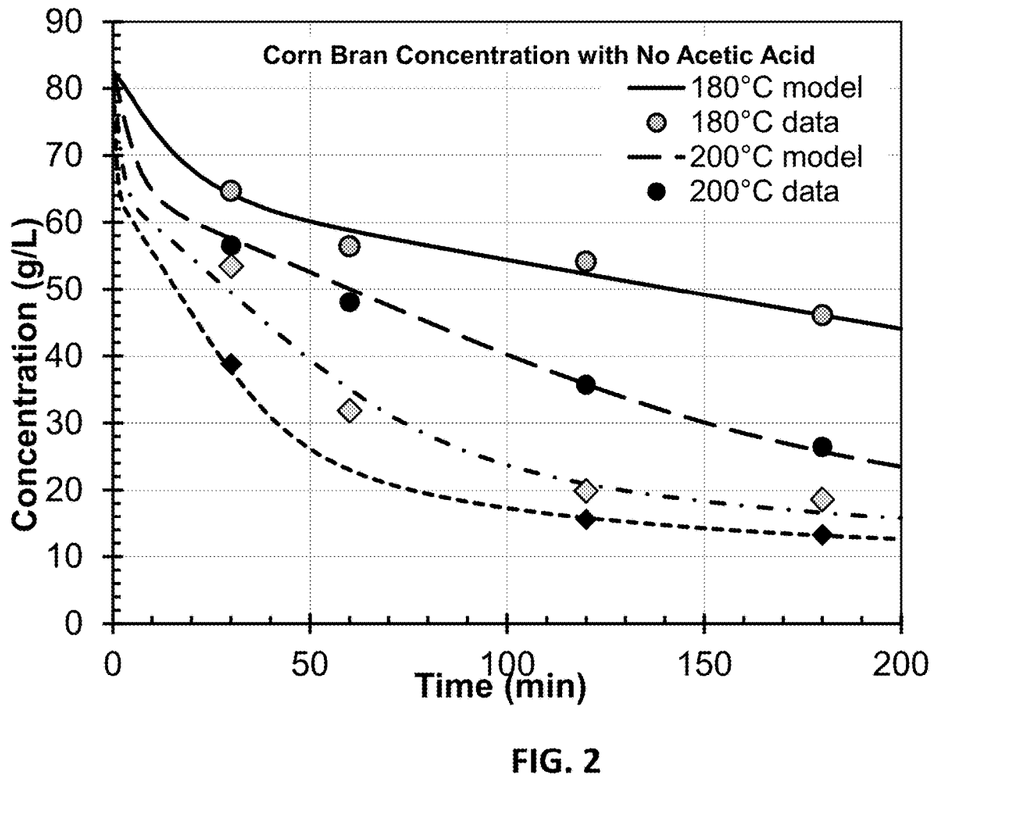
FIG. 2 is a graph showing corn bran concentration as a function of time without using an organic acid and at different temperatures.
Figure 3:
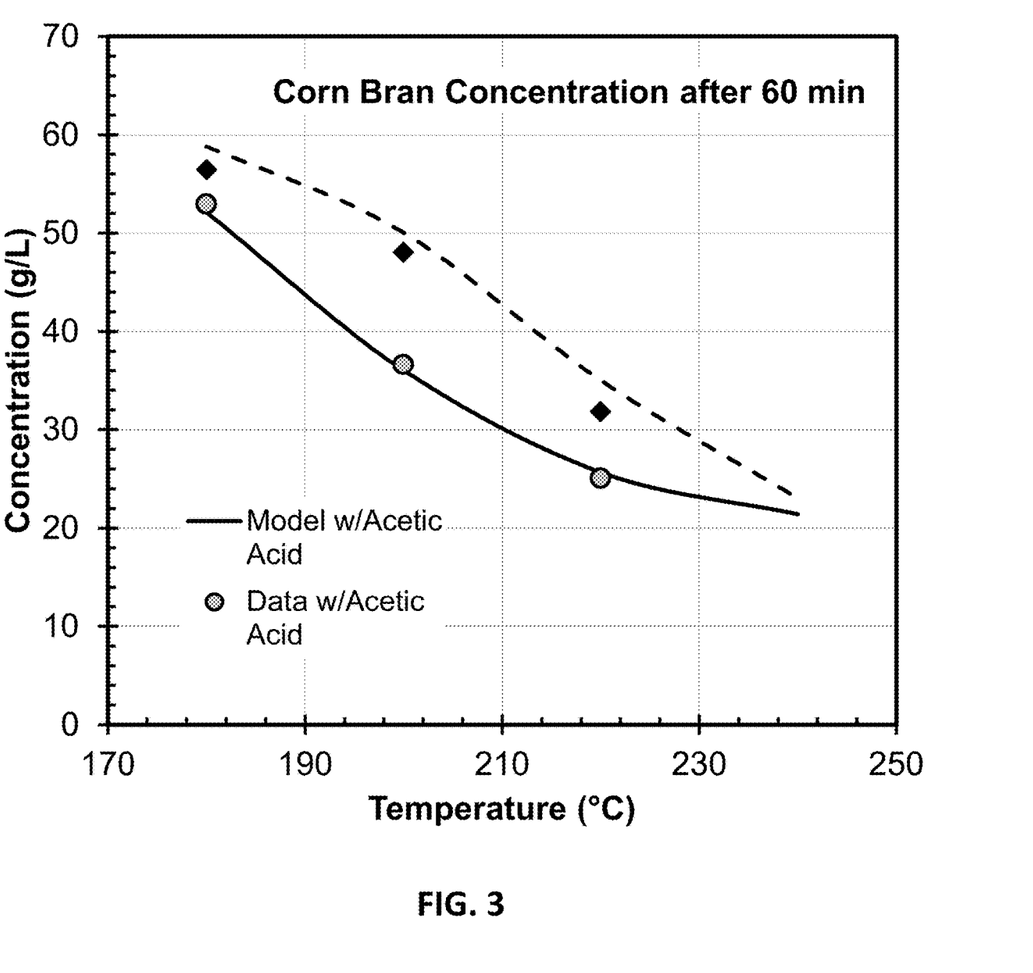
FIG. 3 is a graph showing corn bran concentration as a function of time and that compares corn bran concentration with an organic acid and without an organic acid.

In this example, a series of hot water extraction and acetic acid-catalyzed extractions of hemicellulose in corn bran were conducted. FIG. 2 shows a graphical illustration of experimental data and modeling results for the hot water extraction. FIG. 3 is a graph showing a comparison for hot water extraction results with and without acetic acid-catalyzed extraction. The data demonstrates that organic acids facilitate accelerating the extraction rate, thereby establishing that organic acids produced during the extraction of pentoses from the hemicellulose source material can be recycled and used in the hot water extraction to promote further pentoses production.

Example 2

In this example, a hemicellulose extraction reactor is used to hydrolyze hemicellulose of a hemicellulose source material into its component sugars while minimizing the hydrolysis of other biopolymers in the hemicellulose source material and side reactions. Three parameters are controlled in this reactor: solids concentration, reactor inlet temperature, and residence time. With corn bran as the hemicellulose source material, the concentration in the hemicellulose extraction reactor feed can be set at 10 wt. %. Washing parameters for residual biomass solids also are described.

The reaction temperature is selected to be high enough to hydrolyze the hemicellulose, but not too high so as to avoid depolymerizing cellulose, starches, lignin, and proteins present in the hemicellulose source material. In this example, the inlet temperature to the hemicellulose extraction reactor is set to 200° C. to promote complete (or near complete) hemicellulose extraction with minimal depolymerization of the cellulose, starch, and lignin.

Autohydrolysis of cellulosic materials can be characterized by a severity parameter, which is given by the following equation and which is a function of the temperature history.

$$S = \log_{10}\left[\int_0^t \exp\left(\frac{T(t) - T_{ref}}{14.75}\right)dt\right], \quad (1)$$

where $T(t)$ is the temperature history of the slurry; $T_{ref}$ is the reference temperature, which typically is set to 100° C.; and t is time in minutes. This severity parameter can be used to determine a residence time in the hemicellulose extraction reactor. In some examples, the severity factor is 4.6 for corn bran materials The products of hydrolysis can include simple sugars as well as soluble oligomers. If oligomers are produced, they can be hydrolyzed and dehydrated in the furfural reactive distillation tower. Table 1 summarizes anticipated yields for hemicellulose hydrolysis using a corn bran feedstock.

TABLE 1

| Component | Yield (g/100 g hemicellulose) |
|---|---|
| Arabinose | 30.5 |
| Xylose | 60.9 |
| Mannose | 1.9 |
| Galactose | 4.8 |
| Glucose | 5.8 |
| Uronic Acid | 9.2 |
| Acetic Acid | 7.5 |

The residual solids comprise cellulose, lignin, protein, and the insoluble portion of the starches. The residual starch found in corn bran can comprise approximately 27 wt. % amylose and 73 wt. % amylopectin. Amylopectin is the more soluble portion of the starch. The insoluble starch is separated from the liquid with the other residual solids For washing the residual biomass solids, a 1:1 wash water to solids ratio (based on weight) can be used.

Example 3

In this example, a dehydration step is described wherein pentoses are dehydrated to furfural using a heterogenous catalyst. A reaction temperature of 200° C. can be used with the solid acid catalyst, which is embedded in a structured packing has a high liquid-vapor surface area, which promotes high mass transfer rates and low byproduct formation. Because the higher temperatures can be used, residence time can be reduced. In some examples using a functionalized SBA-15 catalyst, a pentose conversion of 95% with an 85% furfural selectivity can be achieved. Using a reaction temperature of 200° C., a residence time of 10 minutes can be used. Glucose from the hemicellulose source material can be converted to 2-hydroxymethylfurfural (HMF) in the reactive distillation. In some examples, a hexose conversion of 80% can be obtained in the furfural reactive distillation, with a HMF selectivity of 58%.

In view of the many possible embodiments to which the principles of the present disclosure may be applied, it should be recognized that the illustrated embodiments are only preferred examples and should not be taken as limiting the scope of the disclosure. Rather, the scope is defined by the following claims. We therefore claim as our invention all that comes within the scope and spirit of these claims.

We claim:

1. A method, comprising:
heating a slurry comprising (i) a bran material, a fiber material, or a combination thereof, and (ii) water at a temperature ranging from 150° C. to 245° C. to produce pentoses selected from xylose, arabinose, and/or other sugars from the bran material and/or the fiber material, thereby providing an aqueous mixture of residual bran and/or fiber solids and the pentoses;
recycling any organic acids produced from the bran material and/or the fiber material so as to expose the slurry to the organic acids;
filtering the residual bran and/or fiber solids from the aqueous mixture to thereby isolate an aqueous filtrate comprising the pentoses;
treating the residual bran and/or fiber solids to obtain an animal feedstock;
exposing the aqueous filtrate comprising the pentoses to a heterogeneous catalyst comprising a mesoporous silica support modified with an arene-sulfonic acid or a poly(sulfonic acid) to produce an aqueous furfural-containing composition;
exposing the aqueous furfural-containing composition to steam to promote stripping of furfural-containing vapors from the aqueous furfural-containing composition thus providing a furfural-containing fluid; and
condensing the furfural-containing fluid to provide an aqueous furfural-containing liquid.

2. The method of claim 1, further comprising exposing the furfural-containing liquid to a solvent extraction or azeotropic distillation to isolate furfural from the furfural-containing liquid.

3. The method of claim 1, wherein the method is performed batch-wise or as a continuous method.

4. The method of claim 1, wherein the bran material is corn bran or bran from sorghum, and the fiber material is corn fiber or fiber from sorghum.

5. The method of claim 1, wherein the heterogeneous catalyst is embedded in and/or on a surface of a structured packing component.

6. The method of claim 1, wherein condensing the furfural-containing fluid comprises passing the furfural-containing fluid through a condenser.

7. The method of claim 3, wherein the solvent extraction comprises exposing the aqueous furfural-containing liquid to a solvent.

8. The method of claim 3, further comprising treating a separate aqueous phase produced from the solvent extraction by passing the separate aqueous phase through a solvent stripper to separate any residual solvent that may be present in the separate aqueous phase.

9. The method of claim 1, wherein treating the residual biomass solids comprises washing the residual biomass solids and/or exposing the residual biomass solids to a dewatering device.

10. The method of claim 9, wherein treating further comprises a drying step.

11. The method of claim 1, wherein the method does not comprise adding an extraneous mineral acid to the slurry.

12. A method, comprising:
heating a slurry comprising (i) a bran material, a fiber material, or a combination thereof, and (ii) water at a temperature ranging from 150° C. to 245° C. to produce pentoses selected from xylose, arabinose, and/or other sugars from the bran material and/or the fiber material, thereby providing an aqueous mixture of residual bran and/or fiber solids and the pentoses;
recycling any organic acids produced from the bran material and/or the fiber material so as to expose the slurry to the organic acids;
filtering the residual bran and/or fiber solids from the aqueous mixture to thereby isolate an aqueous filtrate comprising the pentoses;
treating the residual bran and/or fiber solids to obtain an animal feedstock;
exposing the aqueous filtrate comprising the pentoses to a heterogeneous acid catalyst;
exposing the aqueous furfural-containing composition to steam to promote stripping of furfural-containing vapors from the aqueous furfural-containing composition thus providing a furfural-containing fluid; and
condensing the furfural-containing fluid to provide an aqueous furfural-containing liquid.

* * * * *